(12) United States Patent
Yagi et al.

(10) Patent No.: US 7,766,838 B2
(45) Date of Patent: Aug. 3, 2010

(54) ULTRASONIC PROBE IN BODY CAVITY

(75) Inventors: Tomoyuki Yagi, Kashiwa (JP); Takashi Ito, Abiko (JP); Mikio Izumi, Soka (JP)

(73) Assignee: Hitachi Medical Corporation, Tokyo (JP)

(*) Notice: Subject to any disclaimer, the term of this patent is extended or adjusted under 35 U.S.C. 154(b) by 630 days.

(21) Appl. No.: 10/511,184

(22) PCT Filed: Apr. 3, 2003

(86) PCT No.: PCT/JP03/04287

§ 371 (c)(1),
(2), (4) Date: May 27, 2005

(87) PCT Pub. No.: WO03/086196

PCT Pub. Date: Oct. 23, 2003

(65) Prior Publication Data

US 2006/0058676 A1    Mar. 16, 2006

(30) Foreign Application Priority Data

Apr. 17, 2002    (JP)    ............... 2002-114333

(51) Int. Cl.
*A61B 8/14* (2006.01)
(52) U.S. Cl. .................................... 600/459
(58) Field of Classification Search ......... 600/437–461, 600/300; 604/19, 20; 310/311
See application file for complete search history.

(56) References Cited

U.S. PATENT DOCUMENTS 5,351,691 A * 10/1994 Brommersma .............. 600/462

| 5,569,158 | A | 10/1996 | Suzuki et al. |
| 7,037,269 | B2 * | 5/2006 | Nix et al. ............ 600/459 |
| 2001/0047134 | A1 * | 11/2001 | Holdaway et al. ......... 600/459 |

FOREIGN PATENT DOCUMENTS

| JP | 62-140451 | 9/1987 |
| JP | 62-272222 | 11/1987 |
| JP | 02-271843 | 11/1990 |
| JP | 2-271843 | 11/1990 |
| JP | 5-13408 | 2/1993 |
| JP | 07-116168 | 5/1995 |
| JP | 61854 | 4/1998 |
| JP | 10-262968 | 10/1998 |
| JP | 11-305143 | 11/1999 |
| JP | 2001-224590 | 8/2001 |

\* cited by examiner

*Primary Examiner*—Brian Casler
*Assistant Examiner*—Elmer Chao
(74) *Attorney, Agent, or Firm*—Antonelli, Terry, Stout & Kraus, LLP.

(57) ABSTRACT

To miniaturize a probe, increase the channel number, and improve the flexibility of a flexible section, an ultrasound probe includes a transducer unit having a plurality of channels arranged for transmitting and receiving an ultrasound wave, and flexible circuit board is connected to the respective channels of the transducer unit in which a signal line for supplying a transmission signal and extracting a reception signal to/from transducer unit is provided. The flexible circuit board forms at least two channel blocks which are formed by dividing the plurality of channels and are spirally wound individually.

3 Claims, 9 Drawing Sheets

Fig.12 though the mouth, anus, and the like of a human body. Accordingly, a flexible section which can be freely bent into a complicated shape corresponding to that of the tubular organ being examined, such as an intestinal canal, has been variously devised as mentioned below.

ULTRASONIC PROBE IN BODY CAVITY

TECHNICAL FIELD

The present invention relates to an intracavitary ultrasound probe to be used for inserting a probe inside a body cavity of an object to be examined and by scanning the object with an ultrasound beam.

BACKGROUND OF THE INVENTION

An intracavitary ultrasound probe is designed to observe an esophageal wall, an intestinal wall, and the like from inside by inserting the probe inside the human body through the mouth, anus, and the like of a human body. Accordingly, a flexible section which can be freely bent into a complicated shape corresponding to that of the tubular organ being examined, such as an intestinal canal, has been variously devised as mentioned below.

First, as disclosed in Japanese Patent Publication No. 2790253 (first conventional technique), an ultrasound probe of the electronic scan type includes an ultrasound transducer group in which a transducer array for transmitting and receiving ultrasound is formed by a plurality of transducers and a flexible printed circuit board formed in a longitudinal direction of the transducers at a predetermined angle relative to the ultrasound transducer group, in which an electrode extraction lead for acquiring a signal from each ultrasound transducer of the ultrasound transducer group is formed on one end.

As shown in FIG. 4(a) of the above-referenced patent document, the printed circuit board is formed so that the section in which the ultrasound transducer group is arranged is rectangular, and an electrode extracting section joined with the rectangular section is formed so that the surface electrode pattern is inclined at a certain angle relative to the longitudinal direction of the ultrasound transducer group. At the same time, the outer shape of the printed circuit is carved out, being inclined at a certain angle similar to the pattern. A portion of the circuit board on which the ultrasound transducer group is mounted has adhering sections at both ends, and an adhering section is also provided on one end of the printed circuit board on which the electrode pattern is formed. When the printed circuit is made into a cylindrical shape and the respective adhering sections are adhered with a bond, the electrode pattern is spirally formed and a gap provided between the adhering sections of the printed circuit board is also formed spirally. With this construction, the printed circuit board can be bent without being broken.

Further, as shown in FIG. 8(a) of the above-referenced patent document, the printed circuit board divides the ultrasound transducer group into blocks, and the electrode extracting section of the printed circuit board is lead in directions of θ, −θ, θ, −θ, . . . in turn at each block. By thus forming the ultrasound transducer group and the printed circuit board into a cylindrical shape, the printed circuit board is constructed in a meshed pattern. The end connected with a lead wire is slightly shifted, so that the position of a land attached with the lead wire does not overlap with a land of another printed circuit board in weaving the printed circuit board. Further, the end connected with the lead wire is provided with an adhering section for adhering each of the printed circuit boards. The printed circuit board, being one undivided plate, can be made more flexible by forming it into a meshed pattern.

Next, as disclosed in Japanese Unexamined Utility Model Patent Publication No. Hei. 5-13408 (second conventional technique), an ultrasound sensor is mounted at the end of a flexible body, and a signal from the ultrasound sensor is transmitted to a cable on the end by a flexible printed circuit (FPC). The FPC is provided with a plurality of slits in its longitudinal direction and is wound in its width direction. A coil spring connected to a GND of the ultrasound sensor surrounds it.

However, according to the first conventional technique, the printed circuit board is formed as one plate. Even in the example of block division, the printed circuit boards are adhered to each other and are substantially made into one plate.

Since the printed circuit board is thus formed as one plate, the range of flexibility of the intracavitary probe is limited by a stiffness of the printed circuit board when it is inserted into the object's body cavity; and, due to this limitation in the flexibility, the intracavitary probe cannot be sufficiently bent along a complicatedly curving tubular organ in some cases. Accordingly, there is a possibility that a part of the intracavitary ultrasound probe will touch a wall of the tubular organ so as to cause pain to the object, which has not been considered.

Further, according to the second conventional technique, the plurality of slits are provided on the FPC in the longitudinal direction and are surrounded with a coil spring 7, which occupies extra space. Therefore, this approach has provided an obstacle to the desire for miniaturizing the probe, increasing the number of channels, and improving the flexibility of the flexible section.

Moreover, an ultrasound apparatus is used not only independently for diagnosis, but also with a treatment device. For example, treatment is conducted by irradiating a strong ultrasound to cauterize a cancer cell. When the ultrasound diagnostic apparatus according to the present invention is used with an electronic device, such as a treatment device, it is also necessary to take into consideration the need to deal with noise infiltrating from the electronic device into the ultrasound probe.

SUMMARY OF THE INVENTION

The present invention has been made in consideration of the above-described problems. A first object thereof is to provide an ultrasound probe, which is miniaturized and in which the number of channels is increased, and in which the flexibility of a flexible section thereof is improved.

A second object of the present invention is to provide an ultrasound probe that is constructed in consideration of the need to deal with noise.

A third object of the present invention is to provide an ultrasound probe in which the wires of the ultrasound probe are not disrupted and broken when the probe is bent, and which is easy to insert into and pull out from a body cavity.

The first object is achieved by constructing an ultrasound probe including transducers for transmitting and receiving an ultrasound arranged in the form of an array of a plurality of channels respectively located at several adjacent positions and a flexible circuit board connected to the respective channels of those transducers and on which a signal line for transmitting a transmission signal and extracting a reception signal to/from the transducers is printed in a longitudinal direction of the transducer with a predetermined angle, wherein at least two channel blocks are formed on the flexible circuit board by dividing the plurality of channels, and the respective channel blocks are spirally wound.

Further, the second object is achieved by constructing an ultrasound probe in which the above-described two or more channel blocks formed on the flexible circuit board are surrounded with an insulating material and a first shield material, or with an insulating material that has evaporated on its surface one of a layer of metallic powder of gold, silver, copper, brass, aluminum, and the like or a combination thereof. Further, the second object also can be achieved by arranging a single second shield material for covering the outer circumference of the bundled channel blocks of the flexible circuit board. And further, this second object also can be achieved more effectively by constructing an ultrasound probe in which each channel block formed on the flexible circuit board is covered with an insulating material and a first shield material, or with an insulating material that has evaporated on its surface a layer of metallic powder of gold, silver, copper, brass, aluminum, and the like or a combination thereof, and by further arranging a second single shield material or protective material, or an insulating material that has evaporated on its surface a layer of metallic powder for covering the outer circumference of the bundled channel blocks of the flexible circuit board.

The third object is achieved by providing either a protection material or a second shield material for covering two or more channel blocks bundled on the flexible circuit board, whereby the channel blocks are not disrupted. Further, handling is improved by making the protection layer of a flexible material, whereby the probe becomes easy to grip, and operation thereof becomes easy for an operator by providing a stiff section and a flexible section.

BEST MODE FOR CARRYING OUT THE INVENTION

Hereinafter, various embodiments of the present invention will be described in detail with reference to the accompanying drawings.

Figure 2:
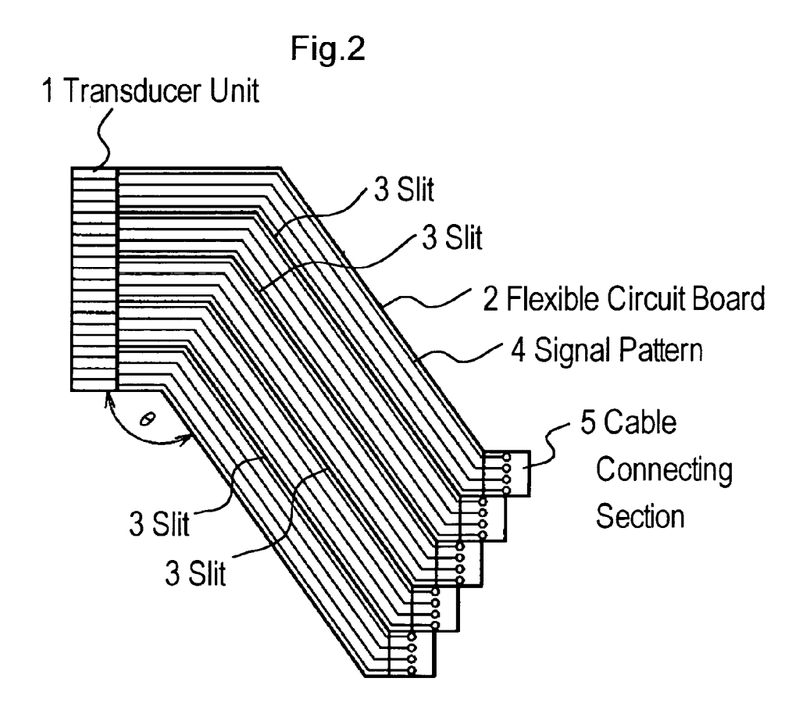
FIG. 2 is a diagram showing a transducer unit of an intracavitary ultrasound probe, a flexible circuit board in which slits are provided, and a joint unit of a cable according to the present invention.

First, an intracavitary ultrasound probe, referred to as a radial type probe, will be taken as an example. FIG. 2 is a diagram showing the connecting relation among a transducer unit, a flexible circuit board, and a cable of the radial type intracavitary ultrasound probe.

Transducer unit 1 is formed so that each transducer element is arranged to correspond with each of a plurality of close positions of transmission and reception (hereinafter referred to as a "channel"). One end of a flexible circuit board 2 is connected to each channel of the transducer elements, and the other end has a cable connecting section 5, so that a signal line can be connected to a cable for transmission and reception. On this flexible circuit board 2, signal pattern 4 is formed so that a signal can be transmitted and received between the transducer unit 1 and the cable connecting section 5, and each signal pattern 4 is electrically insulated. Further, flexible circuit board 2 is not formed by one circuit board, but is formed so that a part of all channels is bundled into blocks divided by a slit 3. Further, it is preferable to provide a ground so as to sandwich the signal pattern 4, because crosstalk in signal transmission can be thereby prevented.

Further, each divided portion of flexible circuit board 2 is spirally wound at an angle θ relative to transducer unit 1. However, because the flexible circuit board is flexible, the angle is not exactly determined, but has a certain range. Accordingly, the slit may be formed roughly at angle θ.

Figure 1:
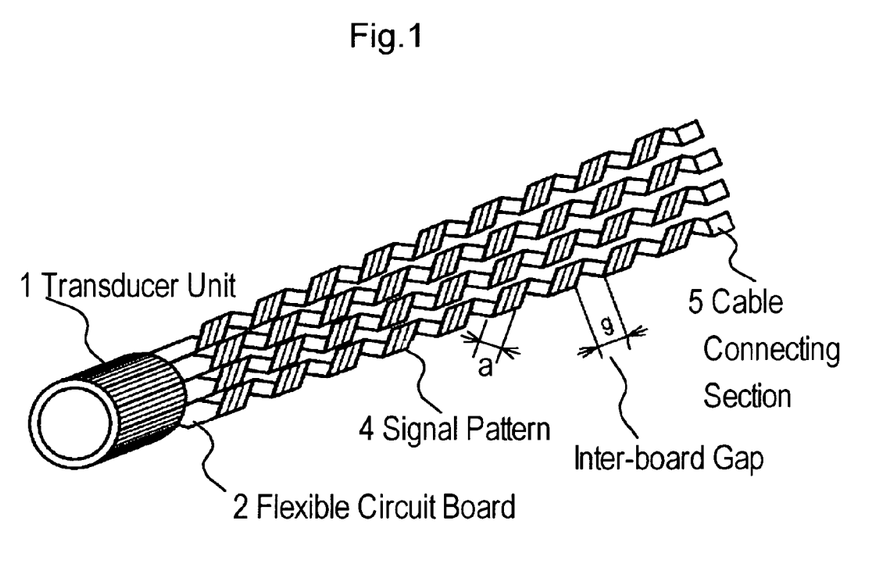
FIG. 1 is a diagram showing the state in which a part of a flexible circuit board of an ultrasound probe according to the present invention is spirally wound.
Figure 3:
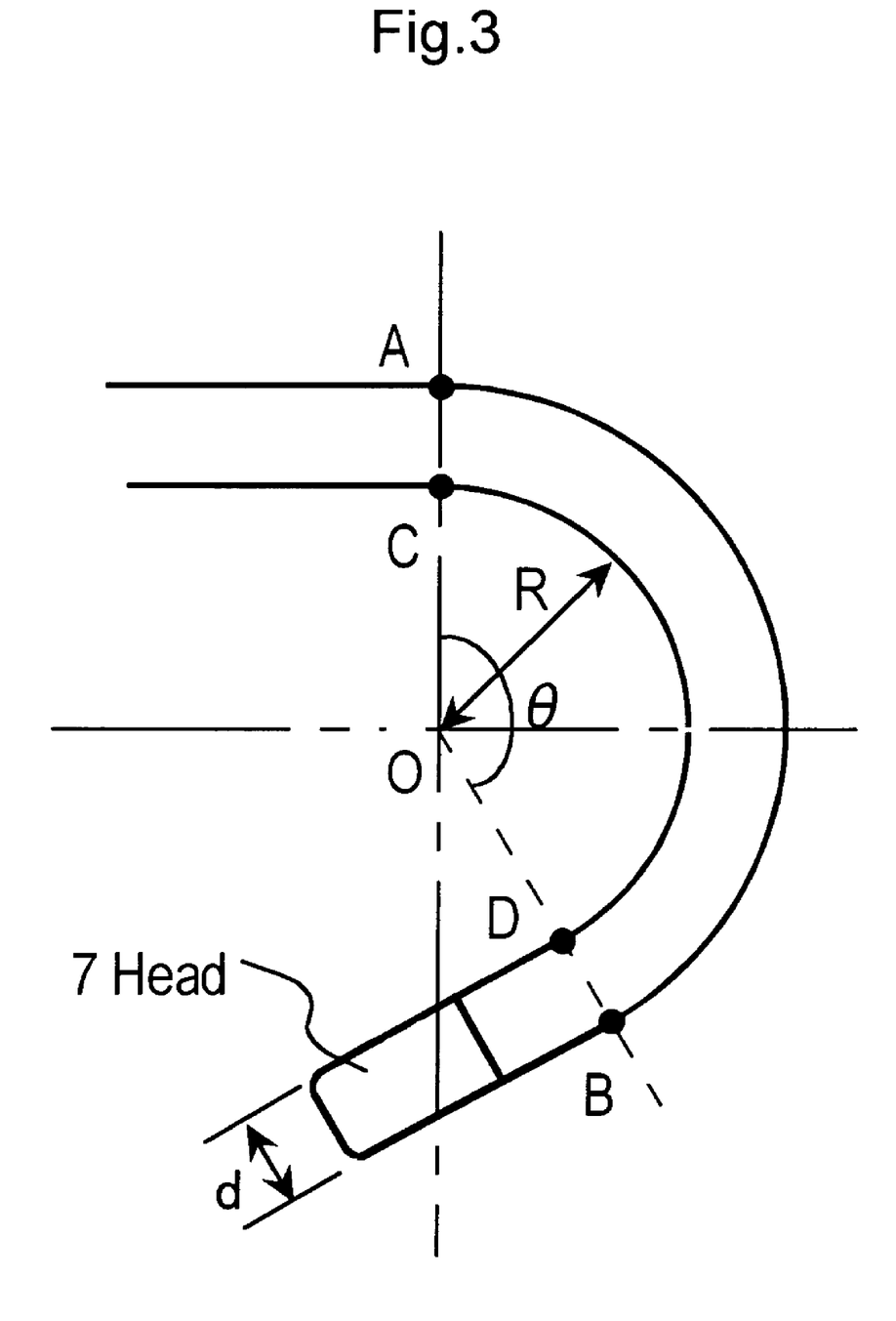
FIG. 3 is a diagram showing the bending state of the flexible intracavitary probe containing the flexible circuit board.

FIG. 1 is a diagram showing the state of the spirally wound flexible circuit board of the intracavitary ultrasound probe according to the present invention. As shown in the figure, transducer unit 1 is rolled and fixed. It may be fixed not only by adhesion, but also by setting it in a formwork and the like. Flexible circuit board 2 is spirally wound at intervals of gap g. At this time, gap g is determined depending on the extent of bending of the body covering the flexible circuit board 2. Here, the principle thereof will be described with reference to FIG. 3. FIG. 3 is a diagram showing the principle for calculating the gap g. When it is hypothesized that the body is bent so as to draw an arc, given that the radius is R, the diameter of the body is d, and the width of one flexible circuit board is a (see FIG. 1), gap g is calculated by formula (1).

$$g+a \cdot d/R \quad (1)$$

A process of deriving this formula will be described. When the flexible section is bent at θ°, as seen in FIG. 3, the length of inner arc CD of the flexible section, which is bent to the maximum, is $2\pi R\theta/360$, and the length of outer arc AB of the flexible section which is bent to the maximum, is $2\pi(R+d)\theta/360$. Accordingly, the difference between outer and inner arcs is $2\pi d\theta/360$. Here, number n of spiral portions in the flexible section (winding number) is calculated by dividing $2\pi R\theta/360$, which is the length of the inner arc of the flexible portion bent to the maximum, by the width a of the flexible circuit board, and the result is $2\pi R\theta/360a$. Gap g is the number obtained by dividing the difference between the arcs of the outer and inner flexible sections by the winding number of the flexible circuit board, which is expressed as $g=ad/R$. Meanwhile, the relation between the width a of the flexible circuit board and the gap g is $a \geq g$.

Figures 4A, 4B:
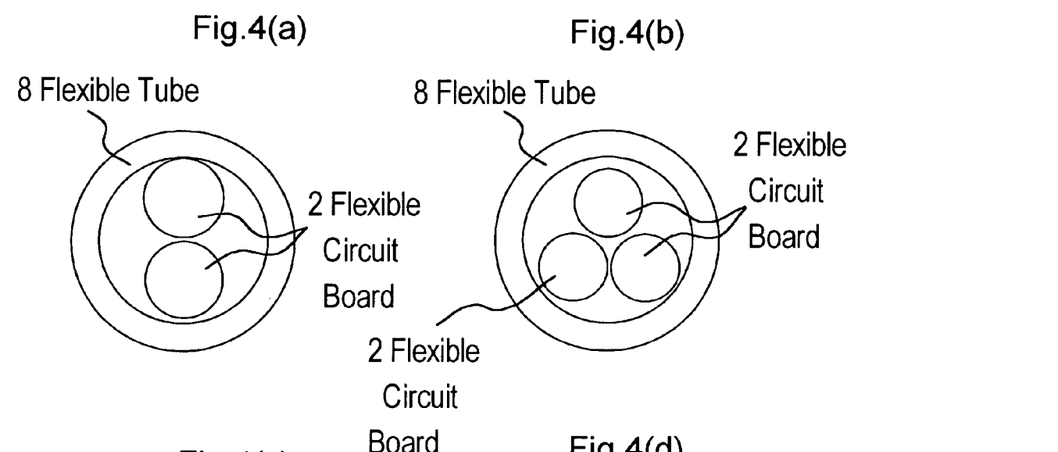
FIGS. 4(a) to 4(d) are diagrams showing examples of the positional relation among a flexible tube used as a protection material for containing a flexible circuit board and the like and a plurality of flexible circuit boards.
Figures 4C, 4D:
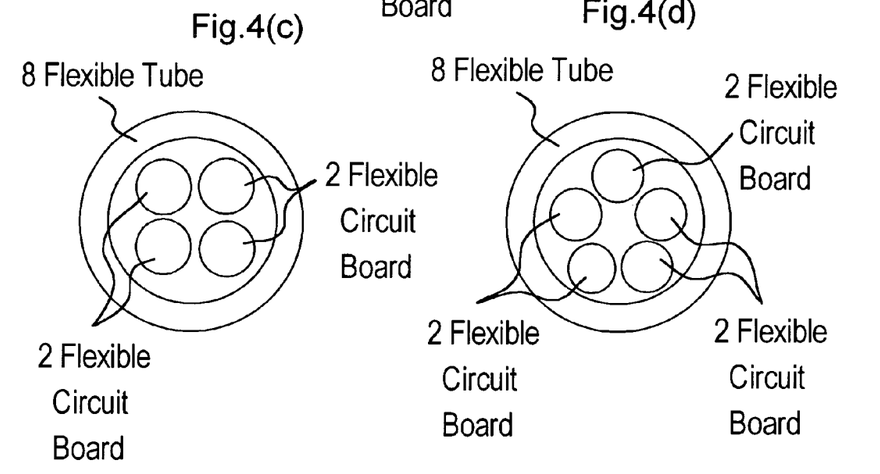

In this manner, gap g of the flexible circuit board 2 is determined, and the flexible circuit board 2 is arranged in a body referred to as a flexible tube made of synthetic resin, synthetic rubber, or the like on the basis of its division number, as shown in the cross sectional views of FIG. 4(a) to FIG. 4(d), which are diagrams showing examples of the arrangement between the flexible tube and a plurality of flexible circuit boards contained therein. FIG. 4(a) shows an example of the flexible circuit board divided into two, each of which is spirally wound. FIG. 4(b) shows an example of a division into three spirally wound flexible circuit boards; FIG. 4(c) shows an example of a division into four spirally wound flexible circuit boards; and FIG. 4(d) shows an example of a division into five spirally wound flexible circuit boards. When the circuit board is divided into six or more spirally wound flexible circuit boards, a close-packed arrangement is formed.

Figure 5A:
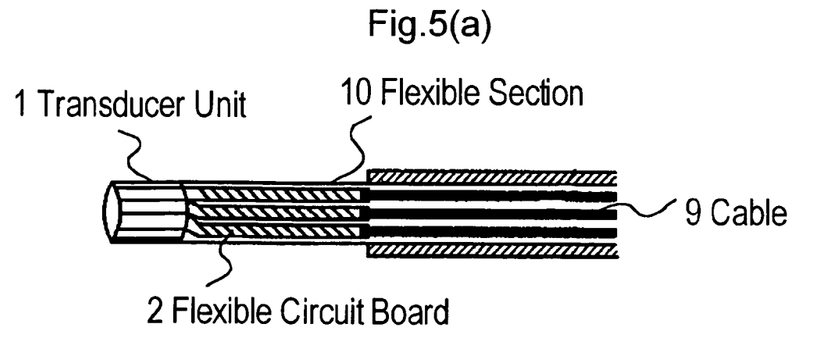
FIGS. 5(a) to 5(c) are diagrams showing the bending state of the flexible circuit board extending from the portion connected with the transducer.
Figure 5B:
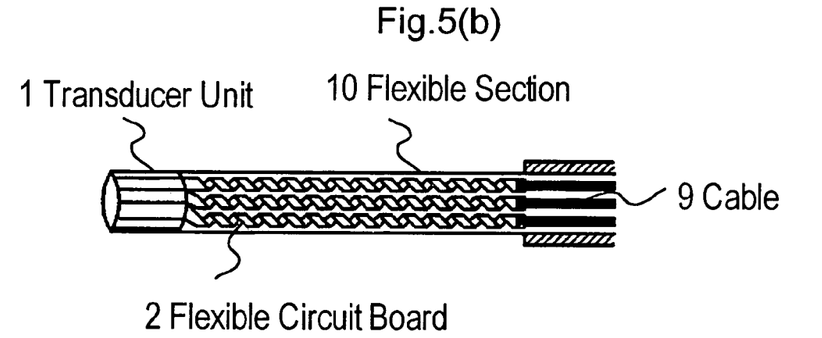
Figure 5C:
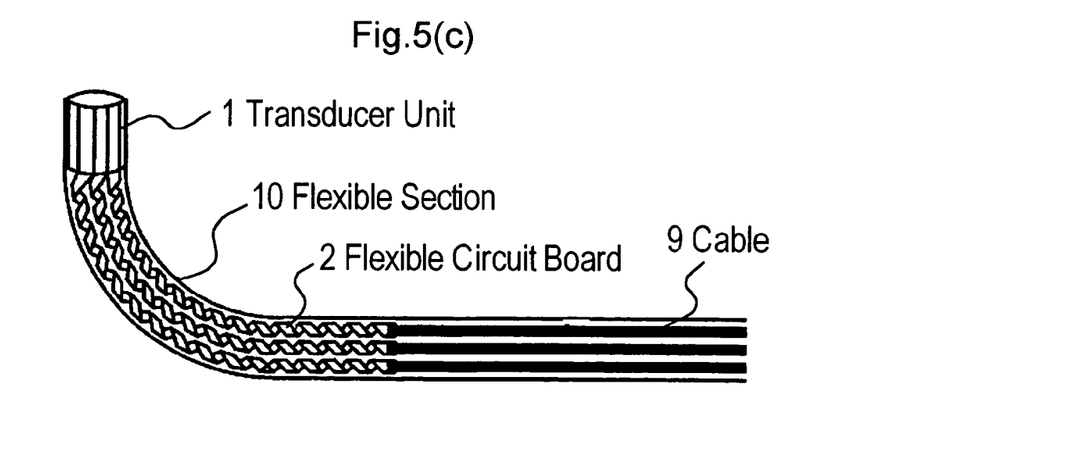

Next, how the flexible circuit board is bent will be described. FIGS. 5(a) to 5(c) are diagrams showing modes of the flexible circuit board from an extraction point (point connected with elements) to a flexible section. The flexible circuit board is contracted as shown in FIG. 5(a) when it does not have to be bent. When it has to be bent, it can be bent as shown in FIG. 5(c), since it has an extensible structure, as shown in FIG. 5(b).

Meanwhile, the intracavitary ultrasound probe includes a convex type, a transesophageal type, and an abdominal type in addition to the radial type, examples of application of which will be mentioned.

Figure 6:
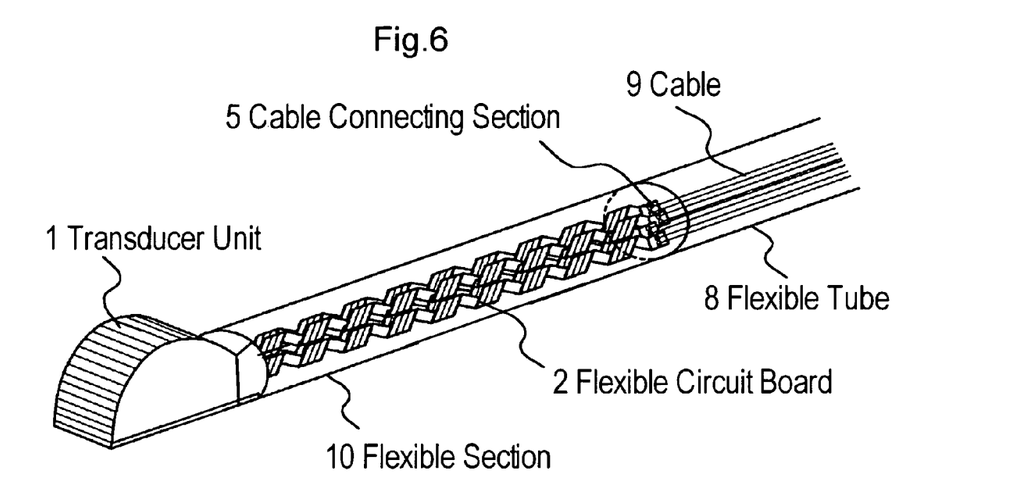
FIG. 6 is a diagram showing an example of the application of the present invention to a convex type ultrasound probe.
Figure 7:
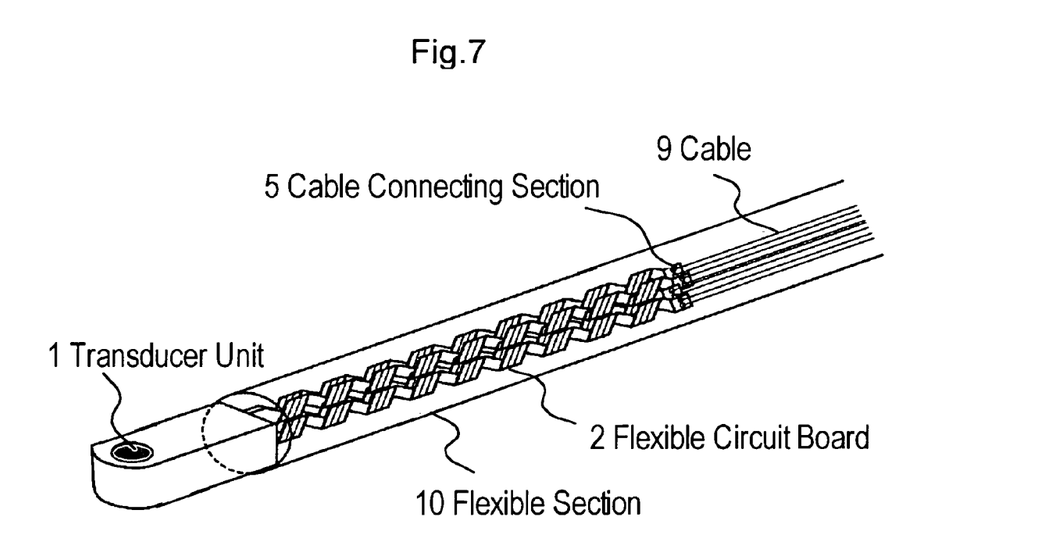
FIG. 7 is a diagram showing an example of the application of the present invention to a transesophageal ultrasound probe.
Figure 8:
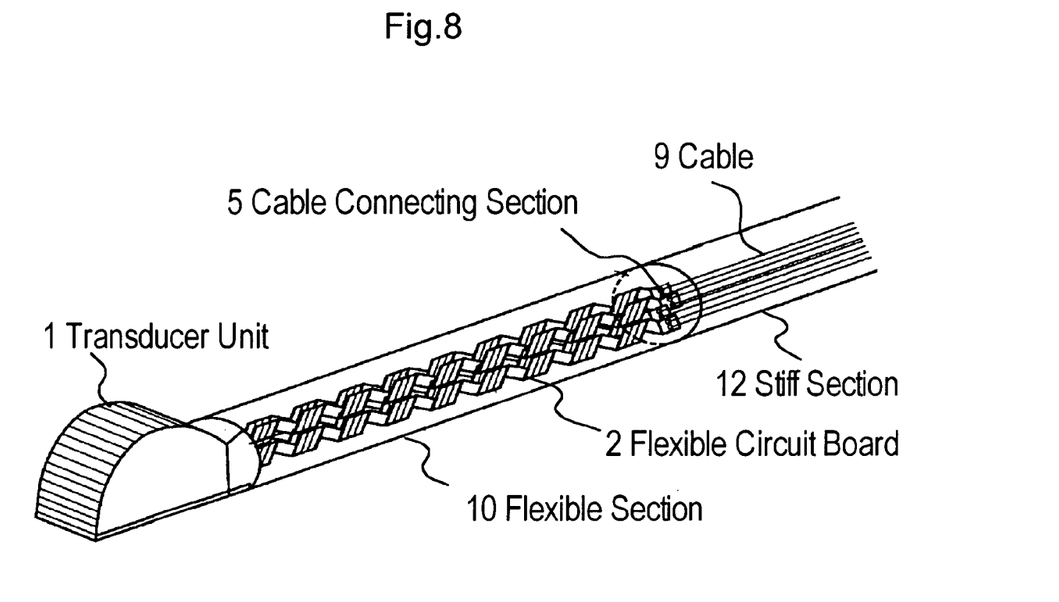
FIG. 8 is a diagram showing an example of the application of the present invention to an abdominal ultrasound probe.

FIG. 6 is a diagram showing an example of application of the present invention to a convex type ultrasound probe; FIG. 7 is a diagram showing an example of application of the present invention to a transesophageal ultrasound probe; and FIG. 8 is a diagram showing an example of application of the present invention to the abdominal ultrasound probe. The radial type probe has a field of view (FOV) in a cross sectional direction of the inner surface of a tubular organ. On the other hand, the convex type probe has a rectangular FOV with respect to an inner wall. As shown in the figure, many probes of the transesophageal type have, e.g. a circular FOV, as shown in FIG. 7, or a polygonal FOV. Although an abdominal type probe also has a rectangular FOV similar to that of the convex type probe, it is not inserted into an object to be examined along a tubular organ, but is inserted into a hole punched on a body surface of the object. Since the probe is difficult to handle if the portion griped by the object is the flexible tube 8, it is made as a hard section 12.

Figure 9A:
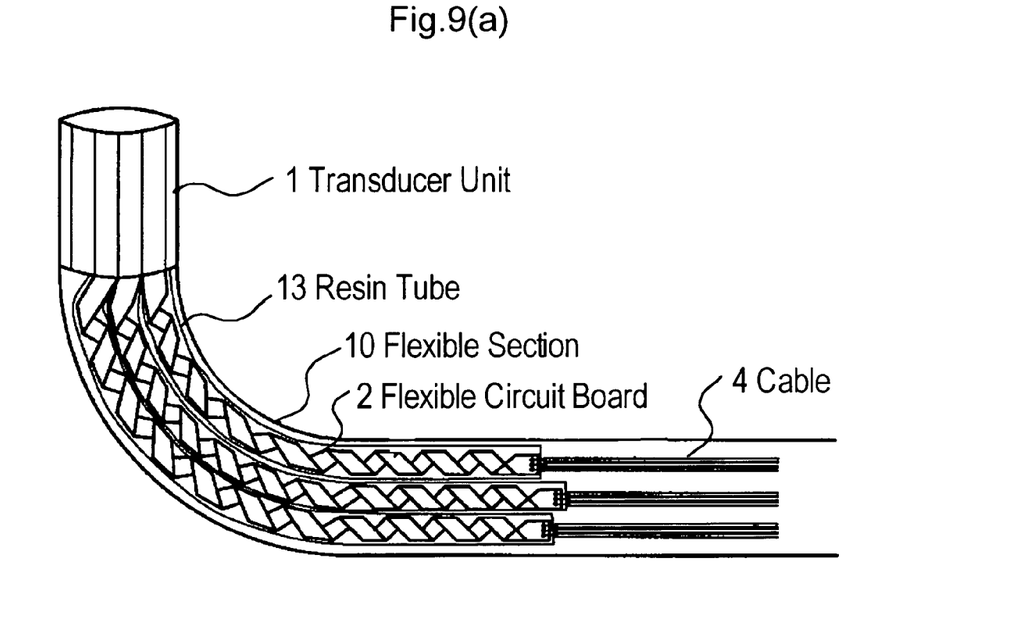
FIG. 9(a) is a diagram showing a perspective view and FIG. 9(b) shows a cross-sectional view of a flexible circuit board covered with a resin tube used as an insulating material.
Figure 9B:
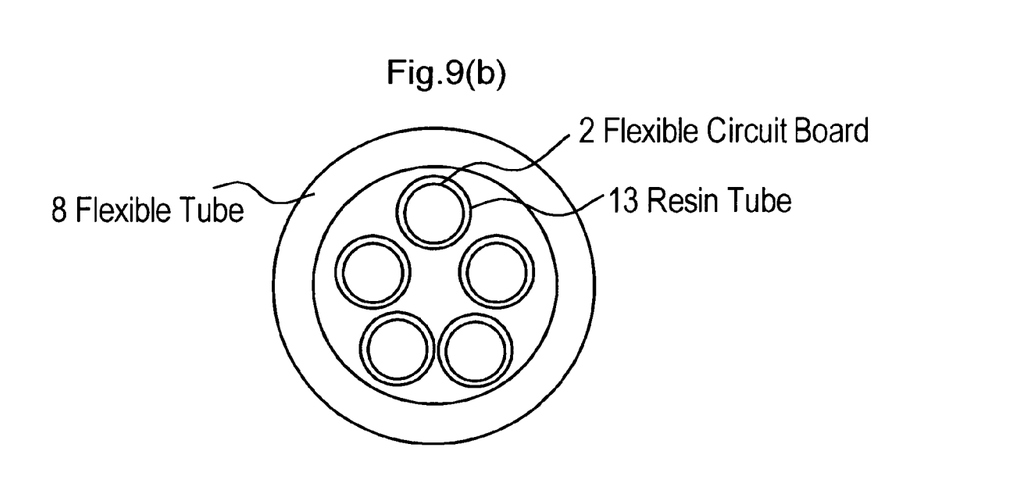

Further, as shown in FIG. 9(a), each of the flexible circuit boards may be individually covered with a resin tube 13 so as to react to bending stress. A cross-sectional view of the body covered with the resin tube 13 is as shown in FIG. 9(b), which shows an example of a division into five spirally wound flexible circuit boards.

Figure 10A:
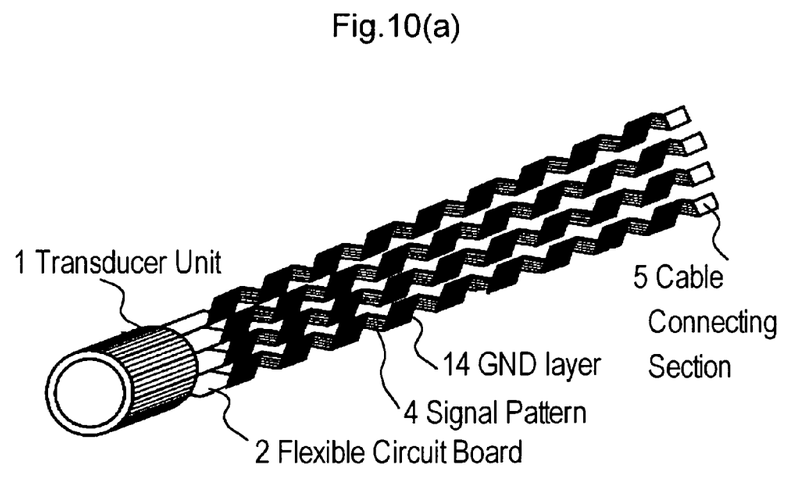
FIG. 10(a) is a diagram showing a perspective view and FIG. 10(b) shows a cross-sectional view of the flexible circuit board formed as a duplex circuit board.
Figure 10B:
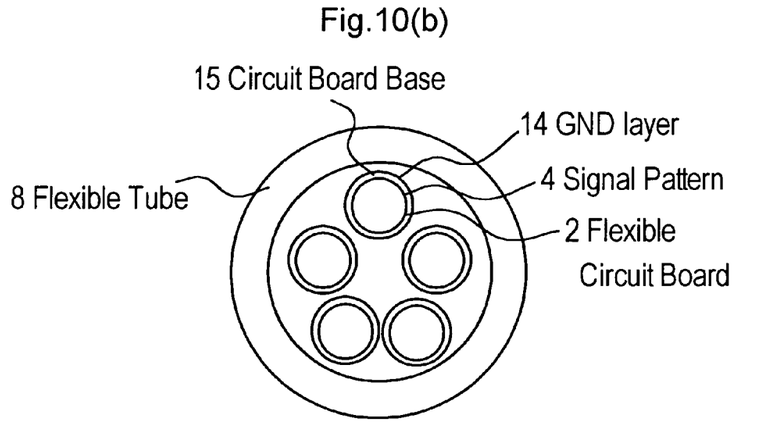

Further, the flexible circuit board is constructed by duplex printed circuit boards, as shown in FIG. 10(a), in which a signal line is connected with one layer and a GND layer 14 is provided over the other layer. Since the pattern of the signal line can be integrated on the signal line layer, this construction is effective in increasing the number of channels and in resolving crosstalk. FIG. 10(b) is a cross sectional view of the body in which the duplex flexible circuit boards are arranged, representing an example of division into five spirally wound flexible circuit boards.

According to the above described embodiment, the limitation of the flexible range of the flexible circuit board (printed circuit board), existing in the state in which the flexible circuit board is made as one plate, is released, the degree of flexibility is properly ensured, and miniaturization of the probe and an increase in the number of channels are enabled, since a coil spring is not used.

Further, the channels of the flexible circuit board may be divided equally or unequally.

Further, since the value of the gap is properly determined, a signal line inside the flexible circuit board is not easily broken.

Further, it is needless to say that the present invention may be applied to a combination of various modes of a flexible circuit board covered with a resin tube, that are formed by two or more multiple layers of a pattern, and the like.

Figure 11:
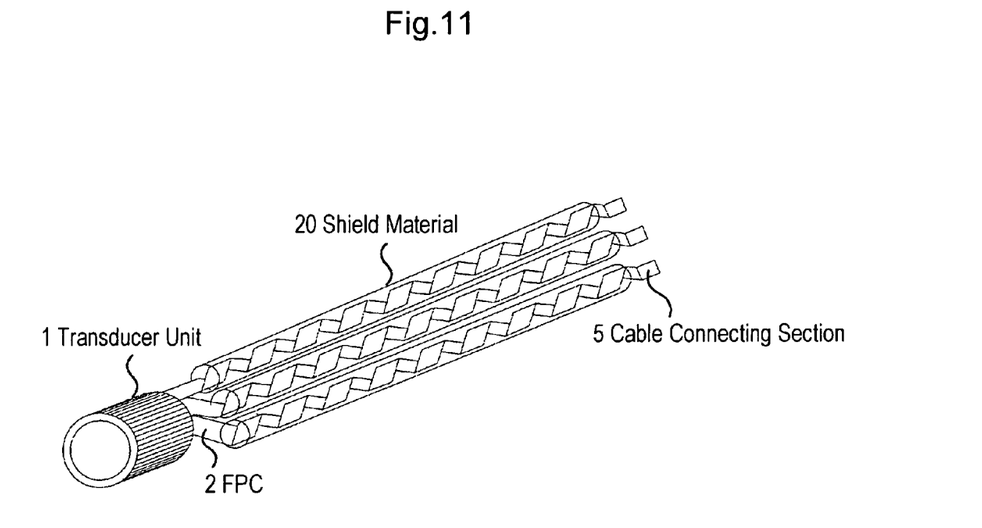
FIG. 11 is a diagram showing an example in which each flexible circuit board is covered with a first shield material.
Figure 12:
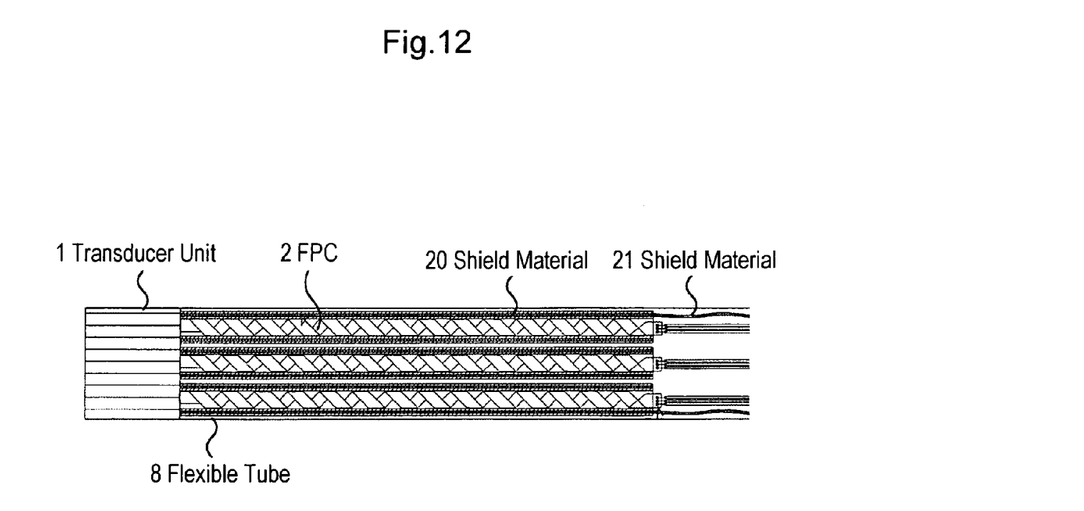
FIG. 12 is a diagram showing a first shield material and a flexible circuit board inserted into the flexible tube used as a protection layer containing parts of FIG. 11, in which the first and second shield materials are electrically connected.

Next, an embodiment involving the use of a shield will be described. FIG. 11 and FIG. 12 show examples of structure of an FPC covered with a shield material.

First, as shown in FIG. 11, transducer unit 1 is made into a cylindrical shape, and each section 2 of the FPC divided by slits is processed into a spiral shape. Each section of a FPC 2 is insulated with a resin tube 13 made of an insulating material. The outside of resin tube 13 is attached with first shield material 20, such as a conductive tape. The shield material is made of a conductive spiral tube or cross tube having a high flexibility and a high shield effect.

Next, as shown in FIG. 12, a set of the FPCs assembled as shown in FIG. 11 is contained within a flexible tube 8 made of a protection material via second shield material 21, which covers the outside of cable. Second shield material 21 may be made of the same material as the first shield member 20, or a braided shield may be used in a coaxial cable. Because both the first shield material 20 and the second shield material 21 are made of a conductive material, they are electrically connected by arranging them so that they touch each other. By connecting the first shield material 20 and the second shield material 21, the shield efficiency is further improved in this construction.

Further, instead of using the above-described first shield material, a metallic powder of gold, silver, copper, brass, aluminum, and the like may be evaporated onto the surface of the resin tube to serve as an insulating material which protects the spiral flexible circuit board.

It is also possible to arrange only the second shield material 21 or the protection material, or both of them on the outer circumference of the spirally wound bundled sections of the above-described flexible circuit board without interposition of the insulating material and first shield material 20. In this case, by evaporating metallic powder of gold, silver, copper, brass, aluminum, or the like onto the surface of the protection material that is used as an insulating material, the protection material can serve as the second shield material.

Further, although a detailed description is omitted, it is needless to say that the present invention is applicable to every kind of intracavitary ultrasound probe, including the convex type ultrasound probe mentioned in conjunction with FIG. 6 and the ultrasound probe mentioned in conjunction with FIG. 7.

As described above, by constructing an ultrasound probe so as to install a shield on a spiral flexible circuit board using a material having a shield effect, it becomes possible to shut off the electromagnetic wave noise affecting an ultrasound image generated by other electronic devices and medical devices used at the same time when a signal is extracted from a transducer to an ultrasound probe, whereby a clear ultrasound image can be provided.

The invention claimed is:
1. An ultrasound probe comprising:
a transducer unit including a plurality of transducers for transmitting and receiving an ultrasound respectively located in correspondence with adjacent positions of transmission and reception; and a flexible circuit board of at least one layer located in correspondence with said positions of transmission and reception, in which signal lines for supplying a transmission signal and for extracting a reception signal to/from said positions are installed;

wherein the flexible circuit board includes a first part which extends from the transducer unit in a longitudinal direction of the plurality of transducers and a second part which is connected to the first part and extends at predetermined angle with respect to the longitudinal direction extension of the first part so as to form a bend at the predetermined angle with respect to the first part;

wherein the flexible circuit board has slits in the longitudinal direction dividing signal lines of the flexible circuit board into a plurality of sections of the flexible circuit board, and each section of the flexible circuit board which is divided by at least one of the slits of the flexible circuit board is individually spirally wound around a longitudinal axis which is different from another longitudinal axis around which another section of the flexible circuit board is individually spirally wound; and wherein a length of the portions of the first part in the longitudinal direction gradually decrease as the portion becomes closer to an inner side of the bend.

2. An ultrasound probe comprising:

a transducer unit including a plurality of transducers for transmitting and receiving an ultrasound; and a flexible circuit board of at least one layer being connected with each of said transducers, in which signal lines for supplying a transmission signal and for extracting a reception signal to/from said plurality of transducers are installed;

wherein the flexible circuit board includes a first part which extends from the transducer unit in a longitudinal direction of the plurality of transducers and a second part which is connected to the first part and extends at predetermined angle with respect to the longitudinal direction extension of the first part so as to form a bend at the predetermined angle with respect to the first part;

wherein the flexible circuit board has slits in the longitudinal direction dividing signal lines of the flexible circuit board into a plurality of sections, and each section of the flexible circuit board which is divided by at least one of the slits of the flexible circuit board is individually spirally wound around a longitudinal axis which is different from another longitudinal axis around which another section of the flexible circuit board is individually spirally wound; and wherein a length of the portions of the first part in the longitudinal direction gradually decrease as the portion becomes closer to an inner side of the bend.

3. An ultrasound probe comprising:

a transducer unit including a plurality of transducers for transmitting and receiving an ultrasound; and a flexible circuit board of at least one layer being connected with each of said transducers, in which signal lines for supplying a transmission signal and for extracting a reception signal to/from said plurality of transducers are installed;

wherein the flexible circuit board includes a first part which extends from the transducer unit in a longitudinal direction of the plurality of transducers and a second part which is connected to the first part and extends at predetermined angle with respect to the longitudinal direction extension of the first part so as to form a bend at the predetermined angle with respect to the first part;

wherein the flexible circuit board has slits in the longitudinal direction dividing signal lines of the flexible circuit board into a plurality of sections, and each section of the flexible circuit board which is divided by at least one of the slits of the flexible circuit board is individually spirally wound around a longitudinal axis which is different from another longitudinal axis around which another section of the flexible circuit board is individually spirally wound; and wherein a member is provided around each spirally wound section of the flexible circuit board.

* * * * *